United States Patent
Kelley

(10) Patent No.: US 11,813,395 B2
(45) Date of Patent: Nov. 14, 2023

(54) CATHETER CONFIGURED FOR USE WITH NEGATIVE PRESSURE AND SYSTEM COMPRISING SAME

(71) Applicant: United States Government as Represented by the Department of Veterans Affairs, Washington, DC (US)

(72) Inventor: Andrew Kelley, Chelmsford, MA (US)

(73) Assignee: United States Government As Represented By The Department Of Veterans Affairs, Washington, DC (US)

( * ) Notice: Subject to any disclaimer, the term of this patent is extended or adjusted under 35 U.S.C. 154(b) by 0 days.

(21) Appl. No.: 16/950,417

(22) Filed: Nov. 17, 2020

(65) Prior Publication Data

US 2021/0146023 A1    May 20, 2021

Related U.S. Application Data

(60) Provisional application No. 62/936,886, filed on Nov. 18, 2019.

(51) Int. Cl.
*A61M 1/00* (2006.01)

(52) U.S. Cl.
CPC ....... *A61M 1/90* (2021.05); *A61M 2202/0496* (2013.01); *A61M 2205/0216* (2013.01); *A61M 2210/167* (2013.01)

(58) Field of Classification Search
CPC .............. A61M 1/90; A61M 1/0023; A61M 2202/0496; A61M 2205/0216;
(Continued)

(56) References Cited

U.S. PATENT DOCUMENTS 3,957,054 A * 5/1976 McFarlane ............ A61M 27/00
                                                            604/541
4,475,910 A * 10/1984 Conway .................. A61F 5/453
                                                            604/352
(Continued)

FOREIGN PATENT DOCUMENTS

WO    WO-2013117635 A1 *  8/2013   ............. A61F 5/453
WO    WO-2017181027 A1 * 10/2017   ........ A61M 37/0015

OTHER PUBLICATIONS

"Determination of the Young's modulus of the epicuticle of the smooth adhesive organs of Carausius morosus using tensile testing", Michael Bennemann, et al., The Journsl of Experimental Biology (2014) 217, 3677-3687 doi:10.1242/jeb.105114 (Year: 2014).*

(Continued)

*Primary Examiner* — Adam Marcetich
(74) *Attorney, Agent, or Firm* — Ballard Spahr LLP

(57) ABSTRACT

An external catheter system can comprise an external catheter comprising an engagement portion that is configured to receive and sealingly engage at least a portion of a penis of a user and an outlet. The system can further comprise a negative pressure source. A conduit can couple the negative pressure source to the external catheter. At least one of the external catheter and the conduit can comprise a portion that, upon application of a negative pressure by the negative pressure source, is configured to collapse to provide a pressure drop between the negative pressure source and the engagement portion of the external catheter.

20 Claims, 5 Drawing Sheets

(58) Field of Classification Search
CPC .. A61M 2210/167; A61M 1/743; A61M 1/87; A61F 5/443; A61F 5/453
See application file for complete search history.

(56) References Cited

U.S. PATENT DOCUMENTS

| | | | | | |
|---|---|---|---|---|---|
| 4,553,968 | A | * | 11/1985 | Komis | A41B 9/023 604/351 |
| 4,713,066 | A | * | 12/1987 | Komis | A61F 5/453 604/351 |
| 4,957,487 | A | * | 9/1990 | Gerow | A61F 5/4405 604/133 |
| 5,195,997 | A | * | 3/1993 | Carns | A61F 5/455 604/347 |
| 5,318,550 | A | * | 6/1994 | Cermak | A61F 5/453 604/350 |
| 5,662,631 | A | * | 9/1997 | Marx | A61F 5/453 604/352 |
| 5,713,880 | A | * | 2/1998 | Anderson | A61F 5/453 604/352 |
| 2004/0006321 | A1 | * | 1/2004 | Cheng | A61F 5/453 604/349 |
| 2004/0230181 | A1 | * | 11/2004 | Cawood | A61F 5/453 604/544 |
| 2005/0101923 | A1 | * | 5/2005 | Elson | A61F 5/453 604/349 |
| 2005/0177133 | A1 | * | 8/2005 | Nielsen | A61F 5/453 604/544 |
| 2005/0275494 | A1 | * | 12/2005 | Gharib | F04B 43/12 335/220 |
| 2006/0004332 | A1 | * | 1/2006 | Marx | A61F 5/453 604/347 |
| 2010/0137775 | A1 | * | 6/2010 | Hu | A61F 13/0256 602/54 |
| 2010/0286667 | A1 | * | 11/2010 | Paz | A61M 25/0017 604/328 |
| 2011/0092927 | A1 | * | 4/2011 | Wilkes | A61F 13/00059 602/42 |
| 2013/0338617 | A1 | * | 12/2013 | Newton, Jr. | A61F 5/453 604/353 |
| 2014/0276633 | A1 | * | 9/2014 | Visveshwara | A61J 15/0003 604/524 |
| 2014/0325746 | A1 | * | 11/2014 | Block | A61F 5/455 4/144.3 |
| 2015/0073361 | A1 | * | 3/2015 | Pratt | A61M 1/882 156/60 |
| 2015/0320583 | A1 | * | 11/2015 | Harvie | A61F 5/441 604/351 |
| 2017/0203017 | A1 | * | 7/2017 | Backes | A61M 1/66 |
| 2018/0345001 | A1 | * | 12/2018 | Heaton | A61M 1/912 |
| 2019/0091059 | A1 | * | 3/2019 | Gabriel | A61F 5/4405 |
| 2019/0151569 | A1 | * | 5/2019 | Fangrow | A61M 5/14546 |
| 2021/0023279 | A1 | * | 1/2021 | Radl | A61M 1/742 |
| 2021/0177643 | A1 | * | 6/2021 | Challa | A61F 5/4408 |
| 2021/0236323 | A1 | * | 8/2021 | Austermann | A61F 5/451 |

OTHER PUBLICATIONS

Supplement Materials of "Determination of the Young's modulus of the epicuticle of the smooth adhesive organs of Carausius morosus using tensile testing", Michael Bennemann, et al., The Journsl of Experimental Biology (2014) 217, 3677-3687 doi:10.1242/jeb. 105114 (Year: 2014).*

"Overview of materials for Silicone Rubber", MatWeb Material Property Data; Https://www.matweb.com/search/DataSheet. Accessed Apr. 7, 2022.*

* cited by examiner (→) indicates urine flow toward suction

CATHETER CONFIGURED FOR USE WITH NEGATIVE PRESSURE AND SYSTEM COMPRISING SAME

CROSS-REFERENCE TO RELATED APPLICATION

This application claims priority to and the benefit of the filing date of U.S. Provisional Patent Application No. 62/936,886, filed Nov. 18, 2019, the entirety of which is hereby incorporated by reference herein.

FIELD

The disclosure relates to urinary catheters and, in particular, to external urinary catheters and catheter systems that are configured for use with negative pressure.

BACKGROUND

According to the Centers for Disease Control, 75% of urinary tract infections (UTIs) are associated with indwelling catheters and between 15-25% of hospitalized patients receive urinary catheters during their stay. External gravity-assisted collection devices such as condom catheters are increasingly utilized in an effort to avoid indwelling catheters. Conventional external gravity-assisted collection devices, an example of which is shown in FIG. 1, have low reliability because of leaking resulting from gaps between the penis and the catheter. The leaking in conventional external gravity-assisted collection devices can result in loss of accurate output measurement. Additionally, conventional external gravity-assisted collection devices can cause skin breakdown as well as painful device removal/replacement. When clinically indicated, such gravity-assisted collection devices are replaced with an indwelling catheter.

SUMMARY

Described herein, in various aspects, is an external catheter system having a negative pressure source. The system can comprise an external catheter comprising an engagement portion that is configured to receive and sealingly engage at least a portion of a penis of a user and an outlet. The system can further comprise a negative pressure source. A conduit can couple the negative pressure source to the external catheter. At least one of the external catheter and the conduit can comprise a portion that, upon application of a negative pressure by the negative pressure source, is configured to collapse to provide a pressure drop between the negative pressure source and the engagement portion of the external catheter.

The portion of the external catheter and/or the conduit that is configured to collapse can comprise a portion of the external catheter between the engagement portion and the outlet.

The conduit can comprises a valve comprising an inlet, an outlet, and a hollow body in communication with the inlet and the outlet of the valve. The hollow body can be configured to collapse upon itself to cause a pressure drop between the inlet and the outlet. The conduit can further comprise a length of tubing in communication with the outlet and the negative pressure source. The portion that is configured to collapse can comprise a hollow body of the valve.

An apparatus can comprise an engagement portion that is configured to receive and sealingly engage at least a portion of a penis of a user, an outlet, and a collapsible portion between the engagement portion and the outlet. Upon application of negative pressure by a negative pressure source in communication with the outlet, the collapsible portion can be configured to collapse to provide a pressure drop between the outlet and the engagement portion.

Additional advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE DRAWINGS

These and other features of the preferred embodiments of the invention will become more apparent in the detailed description in which reference is made to the appended drawings wherein.

DETAILED DESCRIPTION

Figure 1:
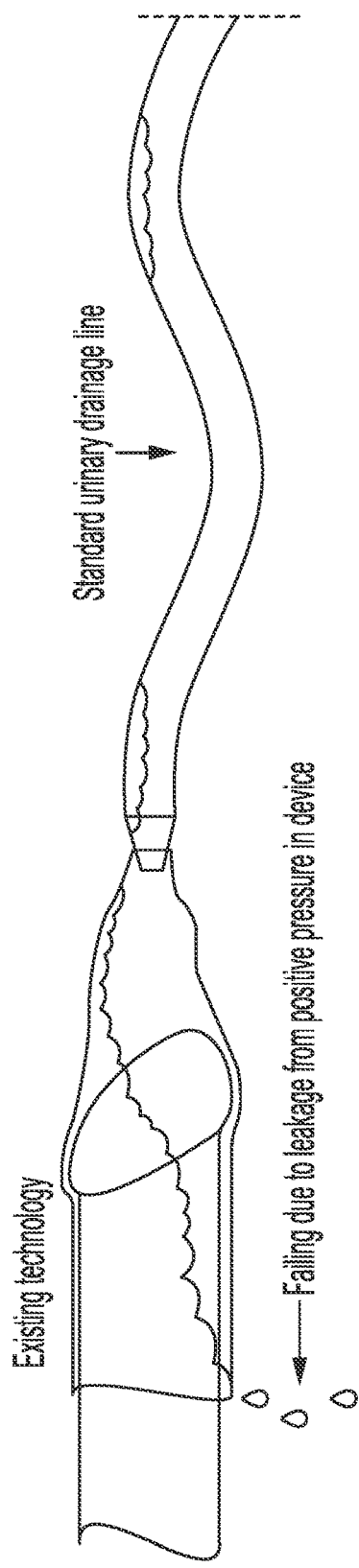
FIG. 1 depicts a prior art system comprising an external (urine) catheter.
Figure 2:
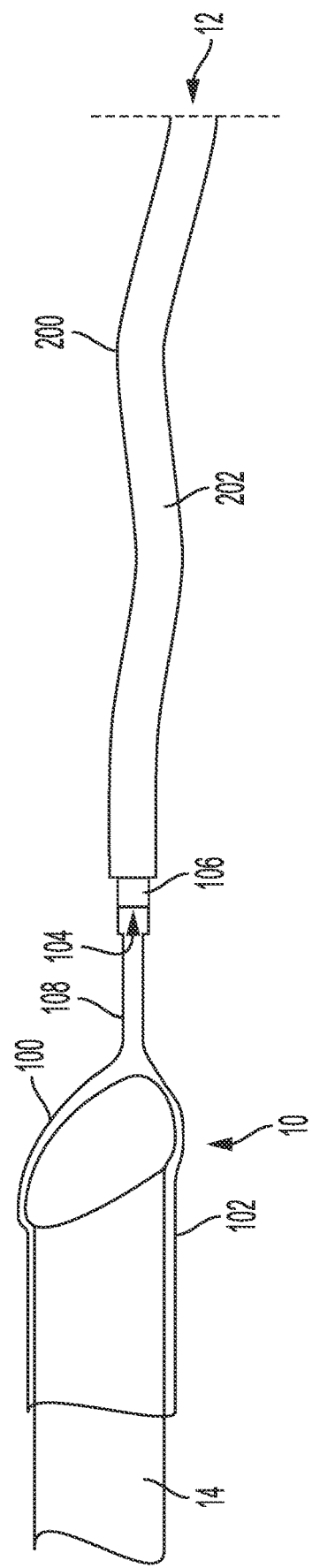
FIG. 2 depicts an external catheter system in accordance with embodiments disclosed herein, showing when the user is not currently urinating.

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. It is to be understood that this invention is not limited to the particular methodology and protocols described, as such may vary. It is also to be understood that the terminology used herein is for the purpose of describing particular embodiments only, and is not intended to limit the scope of the present invention.

Many modifications and other embodiments of the invention set forth herein will come to mind to one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

As used herein the singular forms "a," "an," and "the" include plural referents unless the context clearly dictates otherwise. For example, use of the term "a connector" can refer to one or more of such connectors, and so forth.

All technical and scientific terms used herein have the same meaning as commonly understood to one of ordinary skill in the art to which this invention belongs unless clearly indicated otherwise.

As used herein, the terms "optional" or "optionally" mean that the subsequently described event or circumstance may or may not occur, and that the description includes instances where said event or circumstance occurs and instances where it does not.

As used herein, the term "at least one of" is intended to be synonymous with "one or more of." For example, "at least one of A, B and C" explicitly includes only A, only B, only C, and combinations of each.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Optionally, in some aspects, when values are approximated by use of the antecedent "about," "approximately," or "substantially," it is contemplated that values within up to 15%, up to 10%, up to 5%, or up to 1% (above or below) of the particularly stated value can be included within the scope of those aspects.

The word "or" as used herein means any one member of a particular list and also includes any combination of members of that list.

It is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

The following description supplies specific details in order to provide a thorough understanding. Nevertheless, the skilled artisan would understand that the apparatus, system, and associated methods of using the apparatus can be implemented and used without employing these specific details. Indeed, the apparatus, system, and associated methods can be placed into practice by modifying the illustrated apparatus, system, and associated methods and can be used in conjunction with any other apparatus and techniques conventionally used in the industry.

Disclosed herein, in various aspects and with reference to FIGS. 2-7, is a system 10 comprising an external catheter 100 and a conduit 200. The external catheter 100 can comprise an engagement portion 102 that is configured to sealingly engage a penis 14 of a user. In various aspects, the engagement portion can be provided with various inner diameters in order to ensure a proper fit on the penis. Accordingly, in various aspects, a kit can comprise a plurality of external catheters 100 having different sizes (e.g., small, medium, intermedium, and large). In further aspects, an adhesive can assist in sealingly engaging the engagement portion 102 to the penis. For example, an adhesive can be vulcanized into or otherwise associated with the engagement portion 102, or an adhesive can be used in conjunction with the catheter 100. In still further aspects, a sheath holder can be used to further sealingly engage the engagement portion 102 to the penis 12. The engagement portion 102 of the external catheter 100 can optionally have a similar structure to that of a conventional condom catheter. For example, the engagement portion 102 of the external catheter 100 can be provided in a rolled configuration and can be rolled over the penis to elastically conform to the exterior of the penis. In further optional aspects, the engagement portion 102 of the external catheter 100 can be the same as that of a conventional condom catheter.

The external catheter 100 can comprise an outlet 104 that is configured to couple to a conduit 200 that can be in communication with a negative pressure (i.e., vacuum) source 12. The conduit 200 can comprise, for example, a length of tubing 202. The tubing 202 can optionally comprise or be COVIDEN ARGYLE ¼ inch suction tubing. It is contemplated that ¼ inch tubing can be desirable in that it can be compatible with standard suction containers. The tubing 202 can optionally have flexible ends that can be configured to receive male (typically, rigid) fittings (e.g., fittings of the catheter 100, metal wall suction lines, scopes, etc.). The tubing can optionally be between about 6 and 12 feet long.

The external catheter 100 can optionally comprise silicone, latex, polyurethane, elastomeric polymer, combinations thereof, or other suitable material(s).

The external catheter 100 can optionally couple to the conduit 200 via tubing connections. For example, the external catheter 100 can comprise a barbed male tube fitting 106 that can be received into an inlet end of the length of tubing 202. In these aspects, the barbed male tube fitting 106 can define or at least partially define the outlet 104 of the external catheter 100. The barbed male tube fitting 106 can comprise a material that is sufficiently rigid to be received and retained within the length of tubing 202. In further optional aspects, various other types of tube fittings can be configured to couple the catheter 100 to the conduit 200. In still further aspects, it is contemplated that the external catheter 100 and conduit 200 can be integrally formed or otherwise non-releasably coupled.

The negative pressure source 12 can optionally be a conventional vacuum line outlet of a hospital room. In further embodiments, the negative pressure source 12 can be a stand-alone vacuum pump. In various aspects, the conduit 200 can comprise a collection vessel 206 or container (e.g., a suction canister) that is configured to receive and filter fluid and biomaterial so that the fluid and biomaterial are prevented from entering the negative pressure source 12. Such suction canisters are typically available in most clinical settings (e.g., emergency rooms, intensive care units, and medical/surgical inpatient rooms) and are therefore not described in further detail herein. Thus, the urine received in the collection container can be measured to determine urine output of the user.

Figure 7:
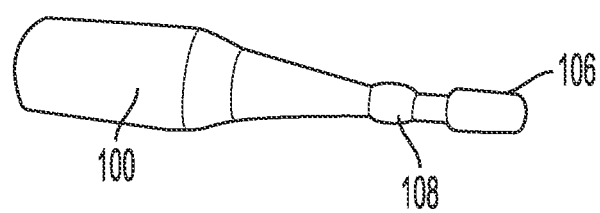
FIG. 7 is a perspective view of an external catheter in accordance with embodiments disclosed herein.

It should be understood that sustained negative pressure (i.e. a differential pressure between the external room pressure and the pressure within the engagement portion of the external catheter) within the engagement portion of the external catheter can lead to tissue irritation or damage. Accordingly, in certain aspects, the external catheter 100 can comprise a collapsible portion 108 that extends from the engagement portion 102 and away from the penis to or toward the outlet 104 and/or the male tube fitting 106. The collapsible portion 108 of the external catheter 100 can be sufficiently flexible and/or elastic so that a pressure within the conduit 200 that is sufficiently less than an external room pressure can cause the collapsible portion 108 to collapse. Referring to FIG. 7, it is contemplated that the collapsible portion 108 can have a larger cross-sectional area (transverse to flow direction) than on opposite sides (relative to the flow direction) of the collapsible portion 108. The larger cross-sectional area can allow the collapsible portion 108 to collapse upon itself. The collapsible portion 108 can collapse so that interior surfaces 110 of the collapsible portion engage (or nearly engage) each other to block (or reduce) flow therethrough, thereby causing a pressure drop between opposing ends of the collapsible portion. In this way, the collapsible portion can provide a pressure drop between the negative pressure source and the engagement portion of the external catheter. The pressure drop can reduce the negative pressure within the engagement portion of the external catheter (i.e. reduce the differential pressure between the external room pressure and the pressure within the engagement portion of the external catheter), thereby minimizing or eliminating tissue irritation or damage.

According to some optional embodiments, the collapsible portion 108 can close entirely or substantially entirely to cause a complete or substantially complete pressure drop between the engagement portion of the external catheter and the vacuum source so that the pressure inside the engagement portion of the external catheter can be equal to, or approximately equal to, the external pressure of the room in which the user is situated (i.e., the external room pressure). In further optional embodiments, the collapsible portion can define small, fluidly communicating portions 112 that can enable the negative pressure source to cause a reduced negative pressure (i.e., a pressure between the external room pressure and negative pressure source pressure) to be provided at the engagement portion 120 of the external catheter 100. The fluidly communicating portions 112 can be formed by the material properties (e.g., the flexibility, as a function of the elastic modulus and thickness of the external catheter material) of the catheter limiting the collapsible portion 108 to seal entirely. In some aspects, it is contemplated that the fluidly communicating portions 112 can be configured to maintain fluid communication so that no barrier is formed to trap urine within the engagement portion of the external condom, and, when the user begins urinating, the collapsible portion 108 more readily opens. In some optional embodiments, the elastic modulus of the collapsible portion 108 can be between 10 kPa and 2000 kPa, or between 20 kPa and 1000 kPa, or about 20-50 kPa. In some optional aspects, the collapsible portion 108 can be configured to cause a pressure differential thereacross of about 50% (e.g., from −200 mmHg to −100 mmHg).

Figure 3:
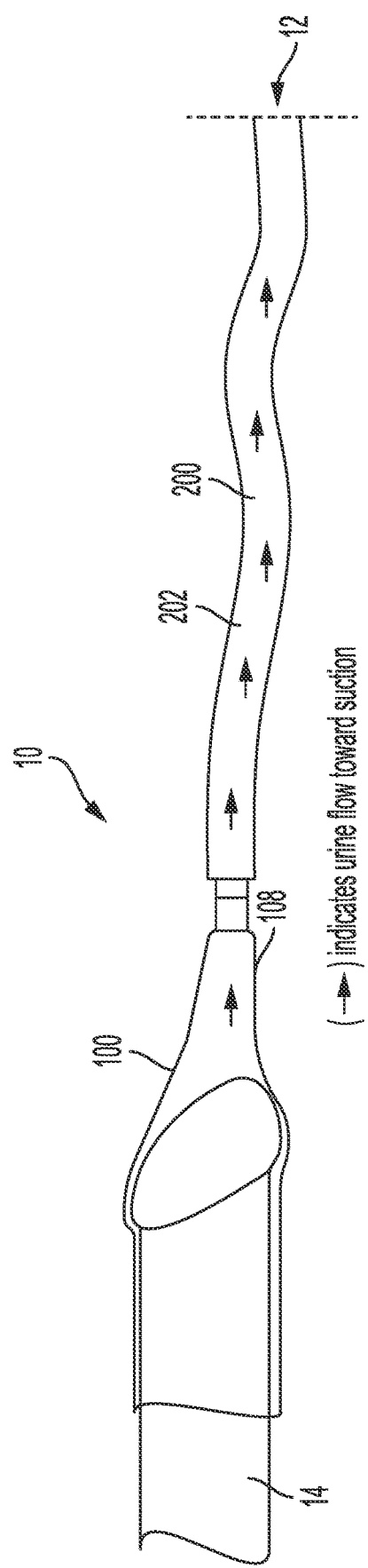
FIG. 3 depicts the external catheter system of FIG. 2, showing when the user is presently urinating.

When the user begins to urinate, the pressure from the urine can cause the collapsible portion 108 to open as shown in FIG. 3. The negative pressure can cause the urine from the catheter to flow through the outlet 104 to remove the urine from the catheter. When the user stops urinating and the urine is removed, or substantially removed, from the catheter, the negative pressure can automatically cause the collapsible portion 108 to collapse and reduce the negative pressure within the engagement portion of the catheter.

Figure 4A:
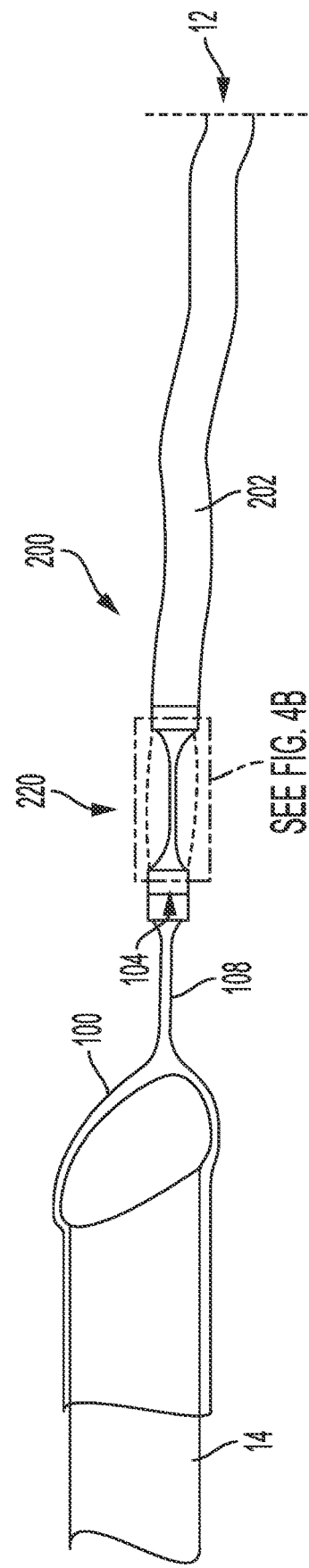
FIG. 4A depicts another embodiment of an external catheter system comprising a valve in the conduit.
Figure 4B:
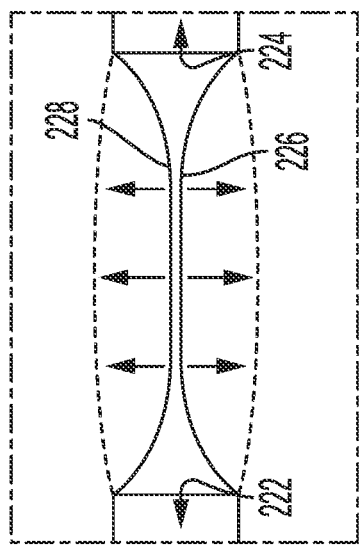
FIG. 4B depicts a close-up of the valve of FIG. 4A.
Figure 5:
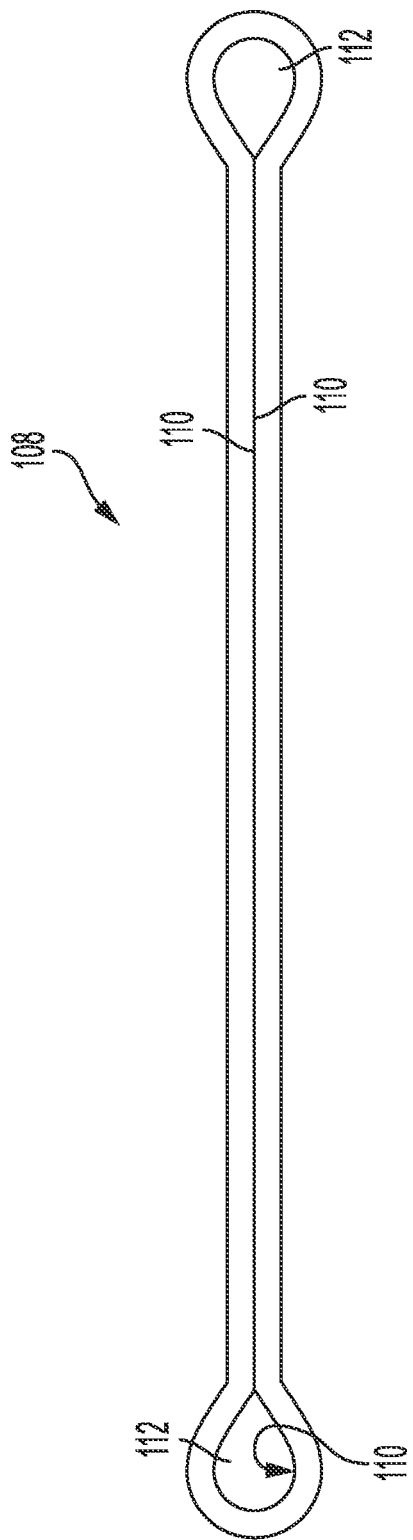
FIG. 5 illustrates a cross section of a collapsible portion of an external catheter.
Figure 6:
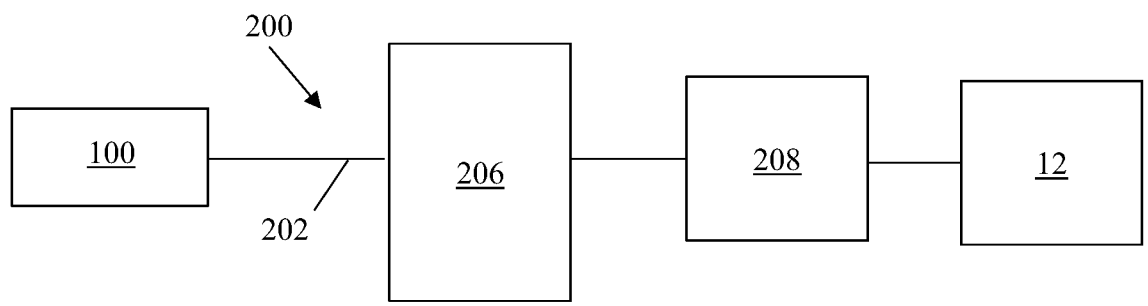
FIG. 6 is a schematic diagram of a system in accordance with embodiments disclosed herein.
Figure 8:
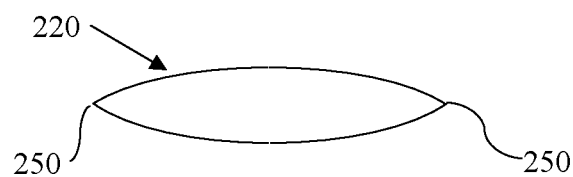
FIG. 8 is an exemplary cross sectional view of the valve as in FIGS. 4A-4B (taken in a plane perpendicular to the direction of urine flow), with the valve shown in an open position.

Optionally, according to further aspects, and with reference to FIGS. 4A-4B and 8, the conduit 200 can comprise a valve 220. The valve 220 can comprise an inlet 222, an outlet 224, and a hollow body 226, comprising a collapsible portion 228, with the hollow body 226 extending between the inlet 222 and the outlet 224. The inlet 222 and outlet 224 can optionally comprise tube fittings that can couple, respectively, to the outlet 104 of the catheter 100 and an inlet of the tube 202.

The collapsible portion 228 of the hollow body 226 can be configured to operate as described with reference to the collapsible portion 108 of the external catheter 100. That is, the walls can be flexible so that a pressure within the collapsible portion 228 of the hollow body 220 that is less than the external room pressure can cause the collapsible portion 228 to collapse, thereby causing a pressure differential between the inlet 222 and the outlet 224. For example, optionally, a negative pressure of less than 60 mmHg, or between 60 mmHg and 80 mmHg, or less than 100 mmHg can be sufficient to cause the collapsible portion 228 to collapse. In some optional embodiments, the elastic modulus of the collapsible portion 228 can be between 10 kPa and 2000 kPa, or between 20 kPa and 1000 kPa, or about 20-50 kPa. It is further contemplated that the valve 200, when collapsed, can define fluidly communicating portions (as described herein with reference to the collapsible portion 108 of the external catheter 100) to inhibit the valve from completely forming a fluid barrier.

Because the compressible portion 228 is not in contact with the skin of the user, a wider range of materials can be used than for the external catheter 100. For example, the compressible portion 228 can comprise silicone, latex, polyurethane, elastomeric polymer, combinations thereof, or other suitable polymer(s) or material(s).

In some embodiments, the collapsible portion 108 of the catheter 100 and the valve 220 of the conduit 200 can each close to collectively and cooperatively reduce the negative pressure within the engagement portion of the catheter. For example, the system 10 can comprise a catheter 100 and a valve 220. The catheter 100 can comprise a collapsible portion 108. In these aspects, the collapsible portion 108 of the catheter 100 can cause a first pressure differential (e.g., 50%, or 100 mmHg), and the valve 220 can further cause a second pressure differential to further minimize the negative pressure applied to the penis. Optionally, cooperatively, the catheter 100 and the valve 220 can substantially entirely or entirely reduce the negative pressure applied to the penis so that the pressure within the catheter 100 is equal or about equal to room pressure. In further embodiments, when the valve 220 is present, the collapsible portion 108 of the catheter can be omitted or eliminated. That is, the catheter can be constructed without a collapsible portion, and the valve 220 can close to independently reduce the negative pressure within the engagement portion of the catheter. Accordingly, it is contemplated that the valve 220 can be incorporated within the conduit of a conventional condom catheter or within a urinary incontinence pouch, such as, for example, a HOLLISTER 9873 urinary incontinence pouch (HOLLISTER INC.). The valve 220 can be, for example, modularly incorporated within the conventional condom catheter or urinary incontinence pouch. In this way, conventional urine systems can be adapted for use with negative pressure to draw urine away from the user. In various optional aspects, opposing ends of the valve 220 can be sufficiently rigid to sealingly receive tubing fittings (e.g., male barbs) to allow the valve 220 to be modularly coupled within a system 10.

In some aspects, it is contemplated that the valve 220 can be configured to cause a pressure differential that is equal to, or substantially equal to, the negative pressure of the negative pressure source so that no or substantially no negative pressure is applied to the penis when the user is not urinating. In these aspects, it is contemplated that, in some optional aspects, the valve 220 can be configured to completely close off. For example, as illustrated in FIG. 8, the valve 220 can be formed having, in cross section (within a plane perpendicular to the flow of urine), a fish-shaped profile (e.g., with opposing arcuate surfaces), having preformed pinched opposing edges 250 to minimize or eliminate fluid communicating portions (as shown at 112 in FIG. 5) when closed. The pre-formed pinched edges 250 can be formed via various methods including using a mold shape with the pre-formed pinched edges 250 or by folding and adhering opposing sides of the valve at the inner edges of the valve.

Thus, the collapsible portions of the catheter 100 and/or the valve 220 can provide automatic reduction of negative pressure against the skin of the user when the user is not urinating. Only when the system begins to fill with urine does/do the collapsible portion(s) of the catheter 100 and/or the valve 220 automatically open to reestablish fluid communication between the negative pressure source and the engagement portion of the catheter.

According to some embodiments, the negative pressure source can provide negative pressure at up to about 200 mmHg. In various embodiments, the negative pressure can be at least 60 mmHg, at least 80 mmHg, between 80 mmHg and 100 mmHg, between 100 mmHg and 120 mmHg, between 120 mmHg and 150 mmHg, between 150 mmHg and 200 mmHg, between 80 mmHg and 200 mmHg, between 100 mmHg and 200 mmHg, or greater than 200 mmHg. In some optional aspects, the negative pressure can be about 100 mmHg. Optionally, the negative pressure can be sufficient to cause collapse of the collapsible portion of the catheter or a valve, as described herein. Accordingly, the negative pressure can be selected based on the material properties of the collapsible portion(s) of the catheter and/or the valve to be sufficient in order to cause collapse of the collapsible portion of the catheter and/or the valve. It is contemplated that a negative pressure within a range between 60 and 200 mmHg or between 80 and 200 mmHg can sufficiently and reliably collapse the collapsible portion of the catheter or valve, yet allow the collapsible portion of the catheter or valve to open upon urination of the user. In exemplary non-limiting aspects, it is contemplated that an actual pressure of 60 to 80 mmHg at the collapsible portion of the catheter or valve can be sufficient to reliably collapse the collapsible portion. In some optional embodiments, a regulator 208 that is communicatively disposed between the negative pressure source 12 and the catheter 100 can be used to select the negative pressure applied to the catheter 100. In further aspects the regulator 208 can be integral to the negative pressure source 12.

The collapsible portions of the catheter 100 and/or the valve 220 can substantially reduce the sustained negative pressure within the engagement portion of the catheter when the user is not urinating. For example, the collapsible portion(s) can reduce the negative pressure by half (e.g., from 200 mmHg to 100 mmHg) or by at least 25% or at least 60%, or at least 80%, or about 100%. In further embodiments, the collapsible portion(s) can reduce the negative pressure within the engagement portion to about 20 mmHg or about 40 mmHg or about 60 mmHg or about 80 mmHg.

In further aspects, the catheter can sealingly engage any skin of the user surrounding the urethra, such as, for example, a retracted penis pouch (e.g., a HOLLISTER 9873 urinary incontinence pouch). That is, the catheter is not limited to condom-like structures sealing against the penis of the user.

Embodiments disclosed herein can reduce or eliminate leaking common in conventional external catheters. In eliminating leaking, the embodiments disclosed herein can collect substantially all output urine and, thus, enable accurate measure of urinary output. Additionally, the removal of urine using negative pressure can prevent urine pooling against the penis of the user, thereby preventing urinary tract infections (UTIs).

Accordingly, disclosed embodiments can serve as a reliable alternative to an indwelling catheter. In preventing the need for an indwelling catheter this device can, in effect, reduce the number of UTIs while also increasing patient and caregiver satisfaction.

Although the foregoing invention has been described in some detail by way of illustration and example for purposes of clarity of understanding, certain changes and modifications may be practiced within the scope of the appended claims.

What is claimed is:

1. A method comprising:
    positioning an external catheter on a penis of a user, the external catheter comprising an outlet and an engagement portion that receives and sealingly engages at least a portion of the penis of the user; and
    coupling a negative pressure source to the outlet of the external catheter,
    wherein the external catheter or a conduit that fluidly couples to the negative pressure source and the outlet of the external catheter comprises a portion that, upon application of negative pressure by the negative pressure source, is configured to collapse to provide a pressure drop between the negative pressure source and the engagement portion of the external catheter that is sufficient to reduce or eliminate tissue irritation or damage.

2. The method of claim 1, further comprising:
    collecting urine from the external catheter.

3. The method of claim 2, wherein urine is received through said portion of the external catheter or said portion of the conduit to cause said portion to open, and wherein said portion collapses upon cessation of receiving urine therethrough.

4. The method of claim 1, wherein the external catheter comprises the portion that, upon application of negative pressure by the negative pressure source, is configured to collapse to provide the pressure drop between the negative pressure source and the engagement portion of the external catheter.

5. The method of claim 4, wherein the portion of the external catheter that is configured to collapse comprises a portion of the external catheter between the engagement portion and the outlet.

6. The method of claim 5, wherein the portion of the external catheter between the engagement portion and the outlet is unitarily formed with the engagement portion of the external catheter.

7. The method of claim 4, wherein the portion of the external catheter that is configured to collapse comprises silicone, latex, or polyurethane.

8. The method of claim 4, wherein the portion of the external catheter that is configured to collapse comprises a material having an elastic modulus of between 10 kPa and 2000 kPa.

9. The method of claim 1, wherein the negative pressure source provides a negative pressure between 60 and 200 mmHg at the outlet of the external catheter.

10. The method of claim 1, further comprising providing the conduit that fluidly couples to the negative pressure source and the outlet of the external catheter, wherein the conduit comprises the portion that, upon application of negative pressure by the negative pressure source, is configured to collapse to provide the pressure drop between the negative pressure source and the engagement portion of the external catheter.

11. The method of claim 10, wherein the conduit comprises:
   a valve comprising:
      an inlet,
      an outlet, and
      a hollow body in communication with the inlet and the outlet of the valve, wherein the hollow body is configured to collapse upon itself to cause a pressure drop between the inlet and the outlet; and
   a length of tubing in communication with the outlet and the negative pressure source, wherein the portion of the conduit that is configured to collapse comprises the hollow body of the valve of the conduit.

12. The method of claim 11, wherein the hollow body comprises pre-formed pinched opposing edges.

13. The method of claim 10, wherein the portion of the conduit that is configured to collapse comprises silicone, latex, or polyurethane.

14. The method of claim 10, wherein the portion of the conduit that is configured to collapse comprises a material having an elastic modulus of between 10 kPa and 2000 kPa.

15. The method of claim 1, further comprising using a regulator to select a negative pressure provided to the external catheter by the negative pressure source.

16. The method of claim 1, wherein the negative pressure source comprises a vacuum line outlet of a hospital room.

17. The method of claim 1, wherein the negative pressure source comprises a vacuum pump.

18. The method of claim 1, wherein the pressure drop is at least 60% of the negative pressure provided by the negative pressure source.

19. The method of claim 1, wherein the pressure drop causes a negative pressure within the engagement portion to be at or below 60 mmHg.

20. The method of claim 1, wherein the pressure drop that the portion is configured to provide is at least 100 mmHg.

* * * * *